(12) United States Patent
Lanzalaco et al.

(10) Patent No.: US 8,815,538 B2
(45) Date of Patent: *Aug. 26, 2014

(54) METHOD OF MAKING COSMETIC COMPOSITIONS CONTAINING A PREBIOTIC

(71) Applicant: The Procter & Gamble Company, Cincinnati, OH (US)

(72) Inventors: Anthony Charles Lanzalaco, Fairfield, OH (US); Duane Larry Charbonneau, Mason, OH (US); Brian Wilson Howard, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/672,192

(22) Filed: Nov. 8, 2012

(65) Prior Publication Data

US 2014/0072533 A1 Mar. 13, 2014

Related U.S. Application Data

(60) Provisional application No. 61/556,892, filed on Nov. 8, 2011.

(51) Int. Cl.
  *C12Q 1/06* (2006.01)
  *C12Q 1/04* (2006.01)
  *A61K 8/00* (2006.01)

(52) U.S. Cl.
  USPC .............................. 435/39; 435/34; 424/401

(58) Field of Classification Search
  USPC ...................... 435/39, 34; 424/401
  See application file for complete search history.

(56) References Cited

U.S. PATENT DOCUMENTS

| | | |
|---|---|---|
| D391,162 S | 2/1998 | Kokenge |
| 6,602,677 B1 | 8/2003 | Wood |
| D516,436 S | 3/2006 | Campbell |
| D535,191 S | 1/2007 | Corker |
| D542,660 S | 5/2007 | Thomas |
| D547,193 S | 7/2007 | Blasko |
| D547,661 S | 7/2007 | Blasko |

(Continued)

FOREIGN PATENT DOCUMENTS

| | | |
|---|---|---|
| DE | 102004013697 A1 | 10/2005 |
| EP | 1050300 A2 | 11/2000 |

(Continued)

OTHER PUBLICATIONS

Yuoff et al., "Application of the BacTiter-Glo Assay for Rapid Enumeration and Screening of Antimicrobial Compounds for *Mycobacterium avium* Complex Bacteria"; 98 Promega Notes 8-10 (2008).

(Continued)

*Primary Examiner* — Rosanne Kosson
(74) *Attorney, Agent, or Firm* — John G. Powell

(57) ABSTRACT

A method for indentifying test agents that exhibit prebiotic activity on human skin commensal microorganisms and cosmetic compositions that include such agents. The method includes providing a test culture of a test agent, a human skin commensal microorganism and a minimal carbon medium. The method provides a time efficient and cost effective way to predict in vivo prebiotic activity of a test agent on skin commensal microorganisms.

18 Claims, 8 Drawing Sheets

| Method | Detection Time | Approximate Detection Limit in cfu/well | | |
|---|---|---|---|---|
| | | S. epidermidis | C. jeikeium | P. acnes |
| ATP | 15 min | 5,000 | 1,500 | 1,500 |
| alamarBlue® | 2 hours | 100,000 | 150,000 | 150,000 |
| LIVE/DEAD® | 15 min | 150,00 | 175,000 | 100,000 |
| Optical Density | 15 min | 5,000,000 | 5,000,000 | 1,500,000 |
| Plate Count | 1-4 days | >10 | >10 | >10 |

(56) References Cited

U.S. PATENT DOCUMENTS

| | | | |
|---|---|---|---|
| D558,591 | S | 1/2008 | Blasko |
| D563,221 | S | 3/2008 | Ashiwa |
| D570,707 | S | 6/2008 | Blasko |
| 2006/0182708 | A1 | 8/2006 | Bockmuhl |
| 2007/0040306 | A1 | 2/2007 | Morel |
| 2007/0190004 | A1 | 8/2007 | Bockmuhl |
| 2007/0205226 | A1 | 9/2007 | Honda |
| 2009/0017080 | A1 | 1/2009 | Tanner |
| 2010/0074872 | A1 | 3/2010 | Blaser |
| 2013/0047361 | A1 | 2/2013 | Steinhardt |
| 2013/0047363 | A1 | 2/2013 | Steinhardt |

FOREIGN PATENT DOCUMENTS

| | | | | |
|---|---|---|---|---|
| EP | 1736537 | A1 * | 12/2006 | ............ C12N 1/20 |
| FR | 2713086 | A1 | 6/1995 | |
| WO | 0120020 | A1 | 3/2001 | |
| WO | 2005033331 | A1 | 4/2005 | |
| WO | 2011022542 | A2 | 2/2011 | |
| WO | 2011065772 | A2 | 6/2011 | |

OTHER PUBLICATIONS

Huiqing Wu et al., "Study on Rapid Quantitative Detection of Total Bacterial Counts by the ATP-Bioluminescence and Application in Probiotic Products", 46 Int'l J. of Food Sci. 921-29 (2011).
Bockmuhl et al., "Prebiotic Cosmetics: An Alternative to Antibacterial Products", 9 IFSCC Magazine 197-00 (2006).
Krutman, "Pre- and Probiotics for Human Skin", 54 J. of Dermatological Sci. 1-5 (2009).
Al-Ghazzewi & R. F. Tester, "Effect of Konjac Glucomannan Hydrolysates and Probiotics on the Growth of the Skin Bacterium *Propionibacterium acnes* In Vitro", 32 Int'l J. of Cosmetic Sci. 139-42 (2009).
Grice, Elizabeth A. & Julia A. Segre, "The Skin Microbiome", 9 Nature Reviews Microbiology 244-53 (2011).
Brune, E et al "Identification of McbR as transcription regulator of aecD and genes involved in methionine and cysteine biosynthesis in *Corynebacterium jeikeim*; Journal of Biotechnology", vol. 151, No. 1 Jan. 10, 2011, pp. 22-29.
C Neal "Catecholamine inotropes as growth factors for *Staphylococcus epidermidis* and other coagulase-negavie staphylococci" FEMS Microbiology Letters, vol. 194, No. 2, Jan. 10, 2001, pp. 163-169.
Apodaca et al., "Regulation of *Trichophyton rubrum* Proteolytic Activity" Infection and Immunity, vol. 57 No. 10 Oct. 1, 1989; pp. 3081-3090.
Hyun-Soo Kim et al., "Genes encoding fibonucleoside hydrolase 1 and 2 from *Corynebacterium ammoniagenes*", Microbiology, vol. 152, No. 4, Apr. 1, 2006.
Hunt, Katerine M. et al. "Human milk oligosaccharides enhance the growth of *Staphylococci*" FASEB Journal, vol. 24, Apr. 2010, Abstract only.
Sakinc T et al. "Effects of D-serine on growth of *Staphylococci* under minimal medium" International Journal of Medical Microbiology; 59th annual meeting of the Deutschen-Gesellschaft-Fur Hygiene und microbiologie, vol. 297, no Suppl. 43, Sep. 1, 2007 p. 124.
Park S-Y et al. "Characterization of GLK, a gene coding for glucose kinase of *Corynebacterium glutamicum*" FEMS Microbiology letters, Willey Blackwell Publishing vol. 188, No. 2, Jan. 1, 2000, pp. 209-215.
International Search Report PCT/US2012/064118. Feb. 25, 2013; 15 pages.
International Search Report PCT/US2012/064121; Feb. 25, 2013; 15 pages.

* cited by examiner

| Method | Detection Time | Approximate Detection Limit in cfu/well | | |
|---|---|---|---|---|
| | | S. epidermidis | C. jeikeium | P. acnes |
| ATP | 15 min | 5,000 | 1,500 | 1,500 |
| alamarBlue® | 2 hours | 100,000 | 150,000 | 150,000 |
| LIVE/DEAD® | 15 min | 150,00 | 175,000 | 100,000 |
| Optical Density | 15 min | 5,000,000 | 5,000,000 | 1,500,000 |
| Plate Count | 1-4 days | >10 | >10 | >10 |

METHOD OF MAKING COSMETIC COMPOSITIONS CONTAINING A PREBIOTIC

CROSS REFERENCE TO RELATED APPLICATION

This application claims the benefit of U.S. Provisional Application No. 61/556,892, filed Nov. 8, 2011.

FIELD OF THE INVENTION

The present invention relates, generally, to a method of making cosmetic compositions, which include agents that display a prebiotic effect on human skin commensal microorganisms. More specifically, the present invention relates to a method of making cosmetic compositions that incorporate prebiotic agents identified by using a minimal carbon media. Another aspect relates to a method of making cosmetic compositions that include broad spectrum prebiotic agents or selective prebiotic agents.

BACKGROUND OF THE INVENTION

Human skin is colonized by a diverse array of microorganisms. Colonization generally begins shortly after birth when an infant is exposed to the maternal microflora and other environmental events that typically lead to the colonization of a previously gnotobiotic human fetus. From the time of initial colonization, human skin remains in a state of flux where the composition of its resident microflora changes over time in response to factors intrinsic and extrinsic to the host.

In general, the microorganisms that colonize human skin may be grouped into three distinct categories: (1) those that are sporadic residents and typically do not proliferate on human skin, (2) those that may proliferate and remain on the skin for relatively short periods of time, and (3) those that may permanently colonize the skin. The members of these three groups may differ with respect to their preferred location on the skin and/or body of a person. Although human skin may be generalized as a cool, acidic, desiccate environment, a variety of microenvironments may be found in various locations on the surface of the skin. For example, the groin, axillary vault, and toe web typically exhibit higher temperature and humidity than other regions of the skin and/or body, which may promote the growth of microorganisms suited for such a microenvironment (e.g. *Staphylococcus aureus* and *Corynebacteria*). In another example, the sebaceous glands typically present on the face, chest, and back of a human may promote the growth of lipophilic microorganisms like *Propionibacterium*. Changes in diet; occupation; clothing choice; or the use of antibiotics, antibacterial soaps, moisturizers, cosmetics, hand sanitizers, and/or other anti-microbial skin products are also known to contribute to the variation observed in the type and/or amount of human skin microflora. Environmental factors like temperature, humidity, and exposure to ultra violet radiation are also known to cause changes in the type and/or amount of human skin microflora. Further, intrinsic host factors such as the host's genome, age, sex, and stage of sexual maturity may influence the state of the human skin microflora.

At least some members of the human skin microbiome provide benefits to their human host, for example, by stimulating the human immune system and/or producing anti-microbial substances. For example, *Staphylococcus epidermidis* has been shown to produce anti-microbial peptides that inhibit *S. aureus* biofilm formation. On the other hand, perturbations which disrupt the delicate balance of the skin microflora may result in undesirable consequences to the host and/or microflora. For example, increased production of free fatty acid byproducts associated with the proliferation of *Propionibacterium acnes* may promote the development of acne. Despite the diversity and/or fluctuations observed in the human microbiome among different individuals, it is believed that some members of the human microbiome may be common among different humans. In this regard, it has been shown that certain organisms typically constitute a significant portion of the human skin microbiome.

To combat any undesirable health and/or cosmetic consequences imposed on the host by the growth and/or activity of certain members of the skin microbiome, a variety of bactericidal agents (e.g., antibiotics) are known in the art. While the use of bactericidal agents may be clinically effective in reducing the symptoms associated with the growth of harmful microorganisms on human skin, there are drawbacks. For example, bactericidal agents such as topical antibiotics, benzoyl peroxide, and azelaic acid tend to affect both the beneficial and undesirable skin microflora indiscriminately. The death or behavioral change in the beneficial skin microflora in turn may lead to further undesirable health and/or cosmetic effects on the host, such as skin irritation. Moreover, certain bactericidal agents, in particular topical antibiotics, may promote antibiotic-resistant microbiota, sometimes referred to as "super bugs."

A more advantageous strategy to combat any undesirable health and/or cosmetic consequence brought about by perturbations that disrupt the balance of the skin microbiota may be to identify agents that exhibit prebiotic activity for those members of the skin microbiome that produce a benefit to the host. Compositions containing such prebiotic agents could then be formulated by combining the prebiotic agent with an acceptable dermatological carrier and used topically. For example, moisturizers, hand and/or body soaps, cosmetics, hand sanitizers, body lotions, and/or other skin products suitable for human use may be formulated to include prebiotic agents. Skin care compositions that include a prebiotic agent may provide a more desirable alternative to conventional bactericidal agents, for example, by reducing the likelihood of skin irritation.

Currently, only a limited number of agents have been identified as exhibiting prebiotic activity on certain members of the human skin microbiome. There is no generally accepted method known in the art for effectively predicting which of the myriad of potential prebiotic agents will exhibit suitable prebiotic activity on skin microflora and be suitable for incorporation into topical skin care compositions. As a result, conventional methods for screening prebiotic agents may employ a difficult, time-consuming, and laborious battery of assays to identify a desired prebiotic agent. Additionally, the rich media used in conventional assays do not provide the desired sensitivity when attempting to detect prebiotic activity related to a particular test agent. In other words, a suitable prebiotic test agent may be overlooked due to the lack of sensitivity of conventional assays.

Those skilled in the art have long sought a suitable high-throughput screening method for identifying agents exhibiting prebiotic activity on members of the human skin microbiome, yet have been unsuccessful in developing such a method due to the variety of problems associated with its development. For example, the variability of the skin microbiota among individuals; expense of the assay; test volumes required for the assays; media choice; choice of cell types; detection sensitivity; difficulty in obtaining consistent data for small volumes of cultures; assay format; and the time required to conduct the assay individually and collectively contribute to the difficulty associated with the development of an industry-suitable, prebiotic high-throughput assay. Even identifying a suitable medium for such an assay is a laborious task due to the unique nutritional and environmental requirements of certain members of the human skin microbiome. In addition, there is desire to develop a tiered assaying methodology incorporating a high thru-put assay in combination with a low thru-put assay that is perhaps directionally more predicative for the commercial, large-scale screening of potential prebiotic compounds for the skin prior to placement of an expensive, time-consuming in vivo test.

Accordingly, there is a need for a method of making a cosmetic composition that includes a prebiotic agent identified by an assay that is relatively fast, inexpensive, and reliable.

SUMMARY OF THE INVENTION

In order to provide a solution to one or more of the problems above, disclosed herein is a method of making a cosmetic composition that includes a prebiotic agent identified using a minimal carbon media. The method comprises providing a first culture comprising a test agent, a quantity of at least one human skin commensal microorganism and a minimal carbon media. The method also comprises determining the metabolite level or replication level of the human skin commensal microorganism of the first culture. The method further comprises identifying the test agent as a prebiotic when the test agent increases the replication level or the metabolite level of the at least one human skin commensal microorganism as compared to a control. The method still further comprises combining a safe and effective amount of the prebiotic agent with a dermatologically acceptable carrier.

Also disclosed is a method of making a cosmetic composition that includes a broad spectrum prebiotic agent identified using a minimal carbon media. The method comprises providing at least two cultures, each culture comprising a test agent, a quantity of a human skin microorganism and a minimal carbon media. The method also comprises determining a metabolite level or a replication level of the human skin commensal microorganism of each culture. The method further comprises identifying the test agent as a broad spectrum prebiotic when the test agent increases the replication level or the metabolite level of the human skin commensal microorganisms of both cultures as compared to a control. The method still further comprises combining a safe and effective amount of the broad spectrum prebiotic agent with a dermatologically acceptable carrier.

Also disclosed is a method of making a cosmetic composition that includes a selective prebiotic agent identified using a minimal carbon media. The method comprises providing at least two cultures, each culture comprising a test agent, a quantity of a human skin microorganism and a minimal carbon media. The method also comprises determining a metabolite level or a replication level of the human skin commensal microorganism of each culture. The method further comprises identifying the test agent as a selective prebiotic when the test agent increases the replication level or the metabolite level of one of the cultures but not the other as compared to a control. The method still further comprises combining a safe and effective amount of the selective prebiotic agent with a dermatologically acceptable carrier.

Also disclosed is a method of making a cosmetic composition that includes a prebiotic agent identified using a high-throughput tiered screening assay. The method comprises providing at least two cultures, each culture comprising a test agent, a quantity of a human skin microorganism and a minimal carbon media. The method also comprises determining a metabolite level or a replication level of the human skin commensal microorganism of each culture. The method further comprises identifying the test agent as a broad spectrum prebiotic when the test agent increases the replication level or the metabolite level of the human skin commensal microorganisms of both cultures as compared to a control. The method still further comprises combining a safe and effective amount of the broad spectrum prebiotic agent with a dermatologically acceptable carrier.

DETAILED DESCRIPTION OF THE INVENTION

Definitions

Figure 1:
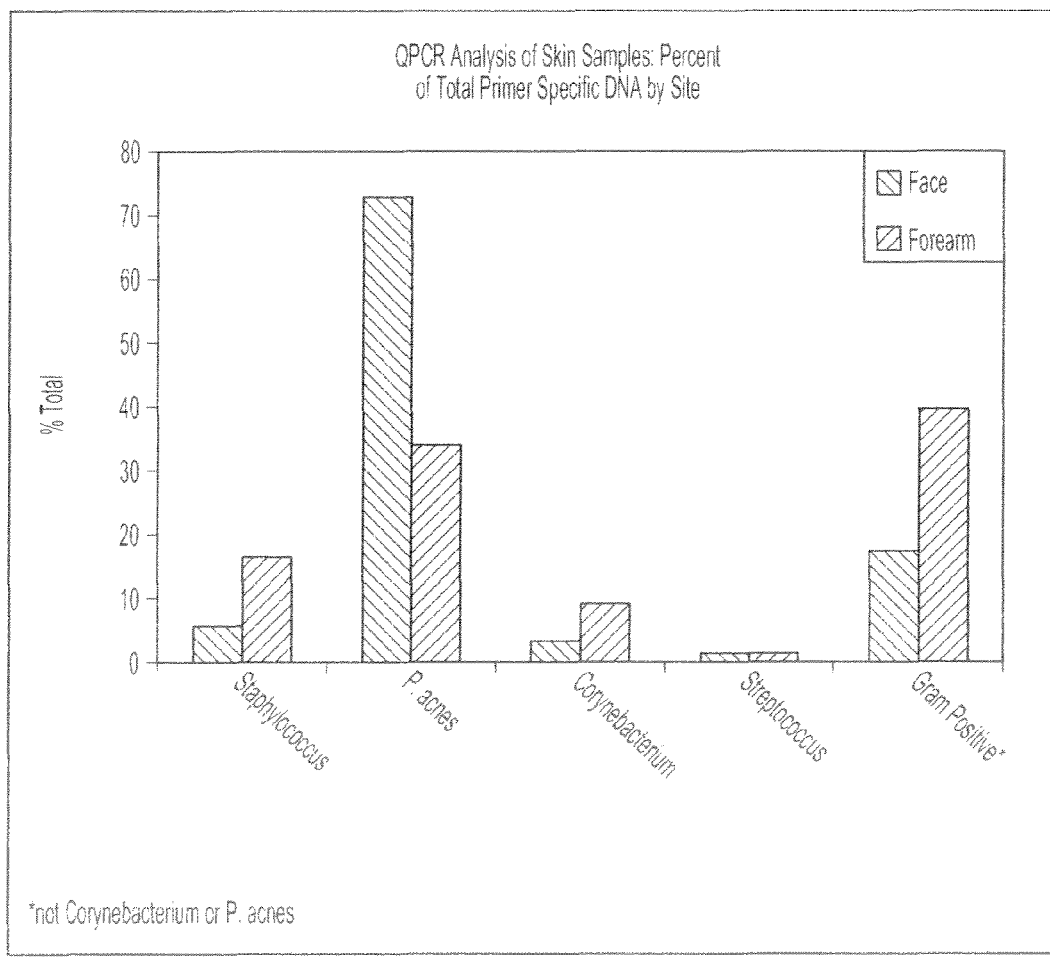
FIG. 1 illustrates an exemplary microbiome population distribution.

"ATP assay" means measuring the adenosine triphosphate ("ATP") level of a test sample to obtain a test value.

"Botanical" means a substance, extract or derivative of a plant.

"Cosmetic composition" means a composition suitable for topical application on mammalian skin and/or other keratinous tissue such as hair and nails. Topical means the surface of the skin or other keratinous tissue. Cosmetic composition includes any color cosmetic, nail, or skin care product. "Skin care" means regulating and/or improving skin condition. Nonlimiting examples of skin care include improving skin appearance and/or feel by providing a smoother, more even appearance and/or feel; reducing the oily and/or shiny appearance of skin. Non-limiting examples of cosmetic compositions include products that leave color on the face, such as foundation, mascara, concealers, eye liners, brow colors, eye shadows, blushers, lip sticks, lip balms, face powders, solid emulsion compact, and the like. "Skin care products" include, but are not limited to, skin creams, moisturizers, lotions, and body washes.

"Dermatologically acceptable carrier" means a carrier that is suitable for topical application to the keratinous tissue, has good aesthetic properties, is compatible with a prebiotic discovered by practicing the present invention and potentially other components, and will not cause any undesirable safety or toxicity concerns. The dermatologically acceptable carrier may be in a wide variety of forms such as, for example, simple solutions (water-based or oil-based), solid forms (e.g. gels or sticks) and emulsions.

"Metabolism" means any chemical reaction occurring inside a microorganism. Metabolism includes anabolism, the synthesis of the biological molecules (e.g. protein synthesis and DNA replication) and catabolism, the breakdown of biological molecules.

"Increase" means increases above basal levels, or as compared to a control.

"Microbial lysate" means the mixture of cellular components and reagents that result from the lysis of a microorganism. "Lysis" involves the action of rupturing the cell wall and/or the cell membrane of a cell by a treatment (e.g. chemical, biological, mechanical, or thermal treatment), resulting in the release of some or all of the cell's biological constituents.

"Microorganism" means bacteria, fungi, algae.

"Minimal carbon media" ("MCM") means a mixture of substances capable of supporting the survival or limited growth of microorganisms (i.e., less than a 0.2 log increase in colony forming units ("CFU") in a 24 hour period) in which carbon is a limiting resource. In certain embodiments, the MCM may be in the form of a liquid or a gel. Because the minimum carbon requirements may vary between different microorganisms, the amount of carbon present in the MCM may also vary. In some embodiments, for example, the MCM may be completely free of carbon. In some embodiments, the MCM may be substantially free of carbon (i.e., less than 0.001% by weight based on the weight of the medium). In some embodiments, the MCM may contain from 0.001% to 0.1% of carbon. The amount of carbon is determined as the mole fraction or molecular weight % of carbon present. For example, glucose is 40% carbon by weight.

"PCR" means polymerase chain reaction and includes real-time PCR, quantitative PCR ("QPCR"), semi-quantitative PCR, and combinations thereof.

"Prebiotic" means any substance or combination of substances that may be utilized as a nutrient by a microorganism, may induce the growth and/or activity of a microorganism, may induce the replication of a microorganism, may be utilized as an energy source by the microorganism, and/or may be utilized by the microorganism for the production of biomolecules (i.e. RNA, DNA, and proteins). Non-limiting examples of prebiotics include mucopolysaccharides, oligosaccharides, polysaccharides, amino acids, vitamins, nutrient precursors, harvested metabolic products of biological organisms, microbial lysates, lipids, and proteins.

"Replication" means the division of a microorganism into daughter cells (e.g. by mitosis or binary fission).

"Selective prebiotic" means a test agent or combination of test agents that increase(s) the metabolism and/or replication of a target species of skin commensal microorganisms, but not of other, non-target species.

"Skin" means the epidermis, dermis, and hypodermis (i.e., subcutis), and also includes the mucosa and skin adenexa, particularly hair follicles, hair roots, hair bulbs, the ventral epithelial layer of the nail bed (lectulus) as well as sebaceous glands and perspiratory glands (eccrine and apocrine).

"Skin commensal microorganisms" means both prokaryotes and eukaryotes that may colonize (i.e., live and multiply on human skin) or temporarily inhabit human skin in vitro, ex vivo and/or in vivo. Exemplary skin commensal microorganisms include, but are not limited to, Alphaproteobacteria, Betaproteobacteria, Gammaproteobacteria, *Propionibacteria, Corynebacteria,* Actinobacteria, *Clostridiales, Lactobacillales, Staphylococcus, Bacillus, Micrococcus, Streptococcus, Bacteroidales, Flavobacteriales, Enterococcus, Pseudomonas, Malassezia, Maydida, Debaroyomyces,* and *Cryptococcus.*

"Test agent" means any synthetic or naturally-occurring element or chemical compound or any recombinantly-produced molecule including, for example, molecules and macromolecules contained or produced in combinatorial libraries or molecules and macromolecules for which the structures were designed by computer or three dimensional analysis. Test agents useful herein also include crude or purified extracts of organic sources (e.g. animal extracts, botanical extracts, and microbial lysates). The test agents herein may be combined with an inert buffer (e.g., saline) or a solvent. Non-limiting examples of suitable solvents include dimethylsulfoxide (DMSO), alcohols such as methanol and ethanol, and aqueous solutions such as water and culture medium.

The articles "a" and "an" are understood to mean one or more of what is being claimed and/or described.

It is to be appreciated that while particular examples recited herein may refer to identifying prebiotics for the skin commensal microorganisms of a human, the methods herein are not limited to such embodiments. The present method may, in fact, be practiced to great advantage in any situation where an assay for identifying a prebiotic is required. It is believed that the detailed description contained herein will allow one skilled in the art to readily adapt the novel method herein to other applications. Additionally, while particular examples may describe the method or portions thereof as being performed manually, one skilled in the art would appreciate that the method or the exemplified portions thereof may be automated.

Selection of Skin Commensal Microorganisms.

The surface of mammalian skin typically includes a wide variety of microorganisms, which may vary from species to species, individual to individual, and even from location to location on an individual. Collectively, the microorganisms on the skin of a person form a microbiome. A healthy skin microbiome will generally consist of a balanced collection of skin commensal microorganisms. The skin microbiome of a person may include a variety of resident microorganisms that help promote the health and/or appearance of the host's skin. But in some instances, certain undesirable microorganisms such as pathogenic bacteria, yeasts and molds may attempt to colonize the skin, which can upset the balance of a healthy microbiome. Fortunately, the resident microorganisms typically present in the skin microbiome have evolved a variety of active and passive mechanisms to inhibit and/or prevent colonization of the skin by undesirable microorganisms. Examples of such passive methods include competing for niches that can be occupied by undesirable microorganisms and consuming nutrients essential for the growth and proliferation of undesirable microorganisms. In terms of active mechanisms, desirable microorganisms may produce metabolites that inhibit the proliferation of undesirable microorganisms, or even kill them outright. In addition to inhibition of undesirable microorganisms, there is a growing body of evidence that certain resident microflora impact innate immunity. For example, it has been demonstrated that certain members of the skin microbiome via their metabolism of lipids, proteins and carbohydrates, produce acid that aids in maintaining the so-called "acid mantel" of the skin.

One approach to maintaining a microbiome in a healthy, balanced state and/or returning a microbiome to a healthy, balanced state may be to provide certain desirable microorganisms with sufficient nutrients to thrive, and thereby out-compete and/or kill the undesirable bacteria. For example, it may be desirable to include one or more prebiotic agents in the compositions used by a person in their daily skin care regimen. However, this is not an easy task because the variability in the makeup of the microorganisms from person to person may render a particular agent suitable as an effective prebiotic for the skin commensal microorganism of one person but not another. Notwithstanding the long-held belief that there is wide variability in the skin commensal microorganisms of different individuals, it has been found that some commonalities do exist.

Since cosmetic skin care compositions are commonly applied to the face, hands and/or forearms of a person, it can be desirable to select human skin commensal microorganisms for an in vitro screening methodology that are sufficiently present on the face, hands and/or forearms of a person to enable in vivo, ex vivo and/or in vitro analysis and comparison, and/or which may positively affect the skin microbiome and/or skin health in the presence of a prebiotic. The microbiome of both the face and forearm of humans has been studied, and it has been determined that *Corynebacterium jeikeium* ("*C. jeikeium*"), *Staphylococcus epidermidis* ("*S. epidermidis*"), and *Propionibacterium acnes* ("*P. acnes*") to varying extents are present in measurable quantities on both the face and forearm such that these microorganisms may be suitable candidates, in certain embodiments, for use in an in vitro screening method.

FIG. 1 illustrates the similar yet diverse microbiome populations that may be present on the face and forearm of a person. The microorganisms illustrated in FIG. 1 were isolated by sampling the skin with a sterile swab wetted with phosphate buffered saline ("PBS"). The QPCR analysis illustrated in FIG. 1 utilized DNA isolated from the swab samples. As shown in FIG. 1, *Staphylococcus*, *Corynebacterium* and *P. acnes* are all present on the face and forearm of the individuals sampled. Thus, the inclusion of *P. acnes*, *Staphylococcus* and *S. epidermidis* in a prebiotic screening method may be particularly useful for predicting the in-vivo effect of a potential prebiotic agent. FIG. 1 also illustrates that *P. acnes* may be more commonly found on the face than the forearm, while the opposite appears to be true for *Corynebacterium* and *Staphylococcus*. Thus, potential prebiotics successfully identified by an in-vitro screening method against *P. acnes* may potentially have a robust impact on skin health and/or the skin microbiome due to their proportionate contribution to the makeup of the forearm and face microbiomes. On the other hand, potential prebiotics successfully identified by an in-vitro screening method against *Corynebacterium* and *Staphylococcus* may be used to provide a targeted skin health benefit specific to the forearms and/or other bodily regions that have a similar microbiome make up.

With regard to skin commensal microorganisms which may positively affect the skin microbiome and/or skin health, it is believed that *C. jeikeium*, *S. epidermidis*, and *P. acnes* provide a skin health and/or desirable microbiome benefit when provided with a compound having prebiotic potential. In particular, it has been demonstrated that *C. jeikeium* produces siderophores that sequester iron. *C. jeikeium* also employs specialized mechanisms for acquiring manganese, both of which are essential for the growth of certain undesirable microorganisms.

*S. epidermidis* is believed to play an active role in stimulating the immune system of the skin, for example, by influencing the innate immune response of keratinocytes through Toll-like receptor ("TLR") signaling. Additionally, *S. epidermidis* is believed to occupy receptors on a host cell that are also recognized by more virulent microorganisms such as *Staphylococcus aureus*. Further, *S. epidermidis* produces lanthionine-containing antibacterial peptides, sometimes referred to as bacteriocins, which are known to exhibit antibacterial properties toward certain species of harmful bacteria. Examples of such peptides include: epidermin, epilancin K7, epilancin 15X Pep5, and staphylococcin 1580. Other peptides produced by *S. epidermidis* counteract intra- and interspecies competitors. The peptides are effective against *Streptococcus aureus*, group A *streptococcus*, and *Streptococcus pyogenes*.

*P. acnes* is a commensal, non-sporulating bacilliform (rod-shaped), gram-positive bacterium found in a variety of locations on the human body including the skin, mouth, urinary tract and areas of the large intestine. *P. acnes* can consume skin oil and produce byproducts such as short-chain fatty acids and propionic acid, which are known to help maintain a healthy skin barrier. Propionibacteria such as *P. acnes* also produce bacteriocins and bacteriocin-like compounds (e.g., propionicin PlG-1, jenseniin G, propionicins SM1, SM2 T1, and acnecin), which are inhibitory toward undesirable lactic acid-producing bacteria, gram-negative bacteria, yeasts, and molds.

Considering the beneficial functions believed to be provided by *C. jeikeium*, *S. epidermidis*, and *P. acnes* and the dominant presence they appear to have on both the forearms and face of a person, it would be desirable to identify agents that exhibit suitable in vivo prebiotic activity for one, two, or even all of these skin commensal microorganisms. While some screening methods described herein may beneficially utilize one or more of *C. jeikeium*, *S. epidermidis*, and *P. acnes*, the screening methods described herein may also be advantageously used with other skin commensal microorganisms.

Minimal Carbon Media.

It is well known that some consumers desire topical products that kill microorganisms on the skin. This desire has lead to a variety of antimicrobial products (e.g., antibacterial soaps, wipes, hard surface cleaners, and the like). When screening a test agent for its antimicrobial properties on a particular microorganism, conventional methods typically employ rich growth media such as, for example, Luria Bertani media, which contains an abundance of the food source typically consumed by the microorganism of interest. It is believed, without being limited by theory, that microorganisms in a rich growth media will thrive, and by testing "well fed" microorganisms the antibiotic activity of a test agent on the microorganism can more easily be observed and/or measured. But because the nutritional requirements of different microorganisms are known to vary, conventional assays may need to use several different rich growth media or media components when screening test agents on different species of microorganism. Preparing several rich growth media for testing may be undesirably costly in terms of time and resources. Perhaps more importantly, the use of microorganisms suspended in a rich growth medium, while suitable for screening test agents for antibiotic activity, may not provide sufficient sensitivity for identifying prebiotic agents. In particular, the rich growth media typically used in conventional assays results in a microorganism that is well fed, and therefore the introduction of a suitable prebiotic agent may induce only a small change or no change at all in a measurable biological indicator such as metabolite level or replication level. The small change or lack of change in the biological indicator may not provide the necessary signal or dynamic range needed to determine prebiotic activity when measured. Thus, when screening test agents for prebiotic activity, it would be desirable to use a single, relatively simple medium that allows a metabolic change induced by the test agent to be easily detectable by the assay used to measure such change.

Contrary to conventional methods, it has been found that minimal carbon media, which can be relatively simple media, are particularly suitable for screening prebiotic agents. In particular, it has been discovered that *C. jeikeium, S. epidermidis*, and *P. acnes* are each capable of surviving in an MCM for up to 72 hours or more (e.g., 96 or 120 hours) while providing sufficient dynamic range to enable effective determination of the prebiotic potential of a test agent. It is believed, without being limited by theory, that the first sign of prebiotic activity on a microorganism is metabolic stimulation such as, for example, an increase in the production of ATP. Thus, measuring ATP levels may be useful for detecting the earliest signs of prebiotic activity on a microorganism, as long as the assay is sensitive enough to detect the changes in ATP in the microorganism.

Figure 2:
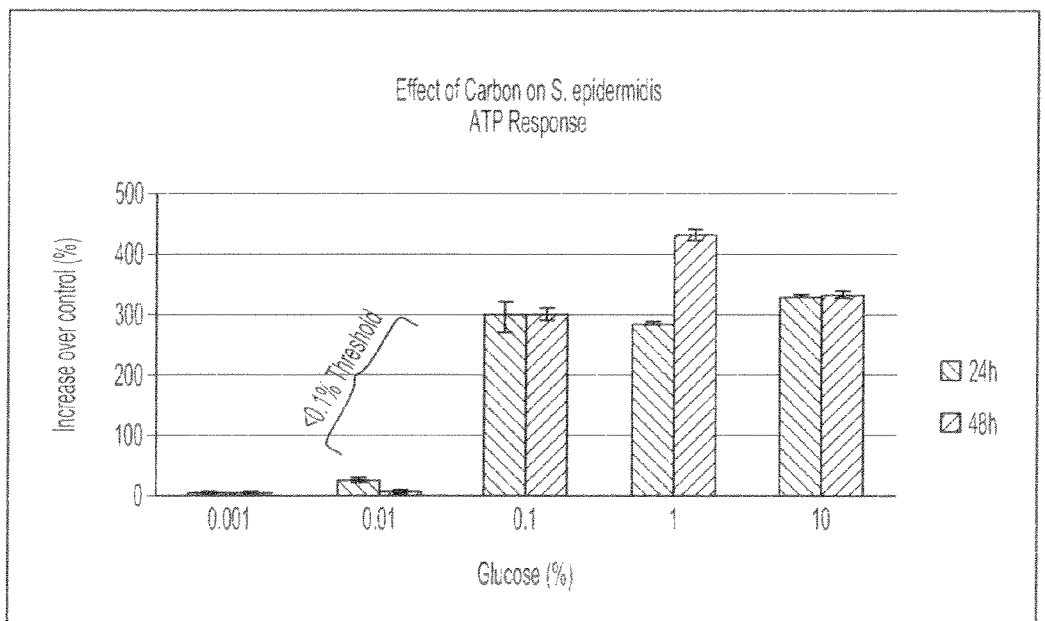
FIG. 2 illustrates the ATP response to various glucose levels for S. epidermidis.
Figure 3:
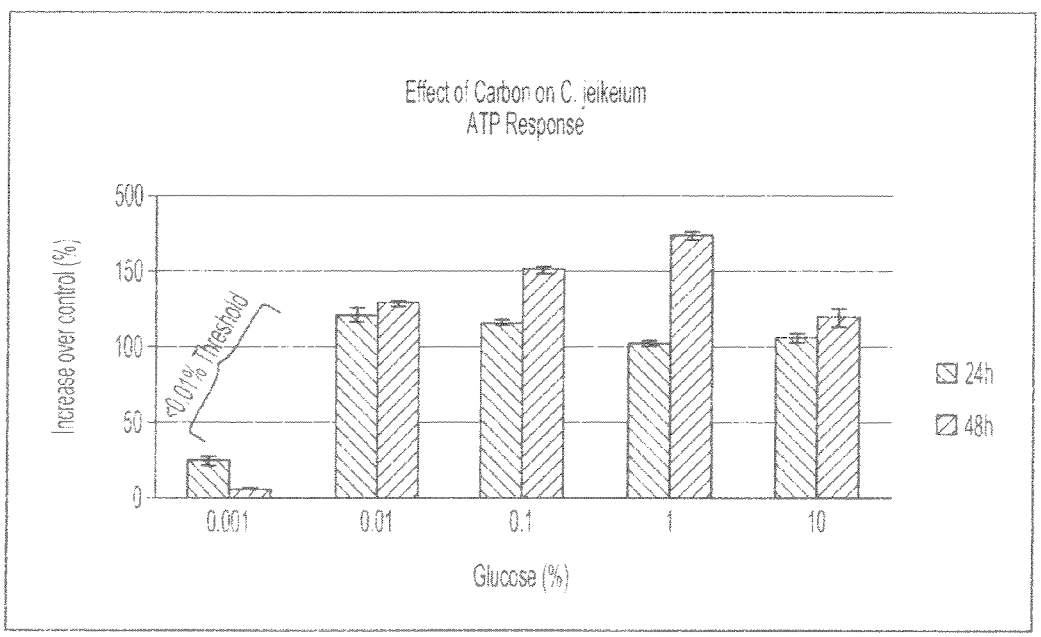
FIG. 3 illustrates the ATP response to various glucose levels for C. jeikeium.
Figure 4:
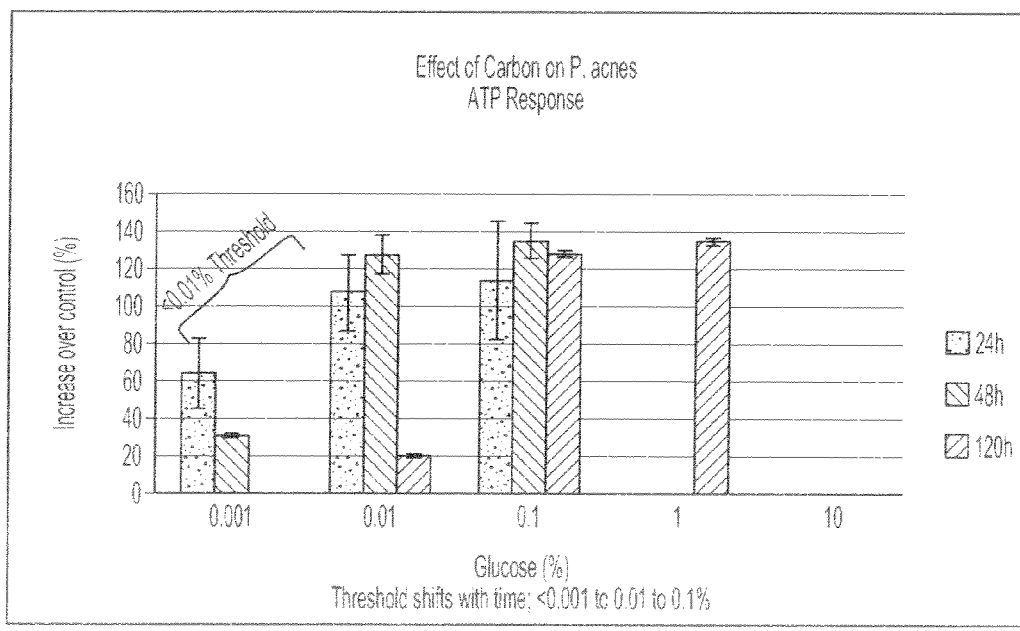
FIG. 4 illustrates the ATP response to various glucose levels for P. acnes.

FIGS. 2 to 4 illustrate a comparison between varying amounts of glucose (i.e., a carbon source) and the dynamic range of detection relative to a water control for *C. jeikeium, S. epidermidis*, and *P. acnes* in an ATP assay. The change in ATP level versus the water control in FIGS. 2 and 3 is shown at 24 hours and 48 hours. The change in ATP level versus the water control in FIG. 4 is shown at 24 hours, 48 hours and 120 hours. As illustrated in FIG. 2, *S. epidermidis* demonstrates a dramatic increase in ATP response at or above 0.1% glucose. Thus, the ability to detect a prebiotic response from a control (i.e., the "dynamic range") can be diminished when using test media that are relatively rich in carbon, which in not uncommon for conventional assays. FIGS. 3 and 4 illustrate a similar response for *C. jeikeium* and *P. acnes*, respectively, although the thresholds are lower. Advantageously, the data illustrated in FIGS. 2 to 4 suggest that *S. epidermidis, C. jeikeium*, and *P. acnes* have minimal carbon thresholds (e.g., <0.1%, <0.01%, and <0.01% glucose, respectively) that are compatible with utilizing a minimal carbon media in conjunction with an in vitro screening method.

It is to be appreciated that while glucose was used to confirm that *C. jeikeium, S. epidermidis*, and *P. acnes* have minimal carbon thresholds and dynamic ranges suitable for use in an in vitro screening method, minimal carbon media suitable for use with the screening methods described herein need not incorporate glucose nor are the thresholds (e.g., <0.01% and <0.1%) of glucose a defining limit for the amount of carbon present in a minimal carbon media.

In addition to providing a single, simple medium for screening prebiotic agents, an MCM may also provide excellent sensitivity. It is believed, without being limited by theory, that by suspending microorganisms in a nutrient poor environment such as an MCM the microorganisms become physically stressed, and the metabolite levels and/or replication levels of the microorganism will not increase over time. In fact, because of the scarcity of a food source in the MCM, the metabolite levels and/or replication levels of the microorganism will eventually decline (e.g., after more than 24 or 48 hours), even though one or both indicators may initially appear relatively stable (i.e., unchanging). Because the metabolite and/or replication levels of the microorganism in the MCM are either decreasing or unchanged over time, any relative increase in one or both indicators resulting from the introduction of a prebiotic agent may be easier to detect, as compared to microorganisms suspended in a nutrient rich environment. It is to be appreciated that a relative increase in an indicator level does not necessarily require an actual increase in the indicator level, but may instead be a slower rate of decline as compared to the indicator level in the MCM. A suitable MCM for use with the novel method herein should permit at least some of the microorganisms in the MCM to survive for at least 48 hours or more, but not thrive. For example, the microorganisms should exhibit less than a 0.2 log increase in the number of CFUs in a 24-hour period of time, but still be present in an amount sufficient to measure the metabolite level and/or replication level at 24 and 48 hours.

In certain embodiments, an MCM may be prepared as a solution of NaCl, $NH_4HPO_4$, $K_2HPO_4$, $MgSO_4.7H2O$, and distilled water. For example, the MCM may be in the form of a solution that includes from 1 to 100 g of NaCl; from 0.1 to 2.0 g of $NH_4HPO_4$; from 0.001 to 1.0 g $K_2HPO_4$; from 0.001-1 g $MgSO_4.7H2O$; and a sufficient amount of distilled water. In a particularly suitable example, the MCM may be a solution formed from 5.0 g NaCl; 1.0 g $NH_4HPO$, 1.0 g $K_2HPO_4$, 0.1 g $MgSO_4.7H2O$, and 500 ml distilled water. The MCM may be optionally supplemented with vitamins, amino acids, iron, biotin, nicotinic acid, D-pantothenic acid, pyridoxal, pyridoxamine dihydrochloride, thiamine hydrochloride, glucose, galactose, mannose, fructose, sucrose, lactose, maltose, and/or combinations of these. In certain embodiments, it may be particularly desirable to prepare the minimal carbon media such that it is free of valine and arginine, which are amino acids essential for growth and which could provide a carbon source (i.e., food) for the microorganism. Prior to using the MCM in testing, the MCM may be sterilized (i.e., free of microorganisms) to avoid adding a source of carbon to the media. The MCM may be sterilized by any suitable method known in the art. For example, the MCM may be passed through a 0.2 µm filter. In certain embodiments, the MCM may be heated to a temperature of 100-120° C., optionally in an autoclave, prior to passing the MCM through the filter. The pH of the MCM should be within a suitable range (e.g., from 6.6 to 7.4, from 6.8 to 7.2, or even 7.0) as this may affect the metabolism and/or doubling time of the microorganisms. The pH of the MCM may be adjusted by adding HCl or NaOH to lower or raise the pH, respectively, during preparation of the MCM.

Referring to FIGS. 5 to 10 and Example 1, discussed in more detail below, dynamic range comparisons of minimal carbon media to rich carbon media for *C. jeikeium, S. epidermidis*, and *P. acnes* for a test compound (e.g., beet pulp) are illustrated. For *C. jeikeium, S. epidermidis*, and *P. acnes*, the beet pulp compound increased the activity of the skin commensal microorganisms as measured by ATP and plate count methods. The minimal carbon media provides a significant dynamic range for *C. jeikeium, S. epidermidis*, and *P. acnes* for screening for compounds having prebiotic potential versus the rich carbon media. Differentiating among test compounds having varying degrees of prebiotic potential (or in some instances no prebiotic potential) would be much more challenging using a rich carbon media.

It is to be appreciated that the minimal carbon media disclosed herein are particularly suitable for use with a wide variety of prebiotic screening methods, including certain methods disclosed herein (e.g., ATP assay and plate count), but other, less preferred media may also be used. Nonlimiting examples of other suitable media may include a highly diluted rich growth medium (e.g., from 10× to 1000×, depending on the microorganism), fermentation broth, or a PBS solution.

Preparation of an Assay Culture

In order to identify a test agent as a prebiotic, it must be shown that the presence of the test agent promotes the survival and/or growth of a microorganism of interest. In certain embodiments, an output of the microorganism that results from exposing the microorganism to the test agent may be measured to determine whether the test agent promotes survival and/or growth. For example, the output may be in the form of a measurable change in the metabolite levels of the microorganism (e.g., ATP, NAD, NADP, NADH, NADPH, cAMP, cGMP, and/or ADP) which are released upon cell lysis. Such metabolic indicators may be measured with a suitable, commercially available enzyme-based assay. Additionally or alternatively, it may be desirable to measure the change in number and/or concentration of the microorganism(s) (i.e., replication level) to determine whether a test agent is a prebiotic.

In some embodiments, the microorganism(s) of interest for use in the novel methods herein may be selected from one or more of the three skin commensal microorganisms discussed above. Additionally or alternatively, the microorganism(s) of interest may be selected by a stochastic method or selected based on particular reasoning. The selected microorganism(s) may be obtained by any suitable manner known in the art. For example, the selected microorganism(s) may be isolated from a natural environment (e.g., the skin of a person) or purchased from a suitable commercial source such as the American Type Culture Collection (ATCC) in Manassas, Va. It is not uncommon for the number or concentration of microorganism(s) obtained by sampling or purchasing to be unsuitable for testing needs (e.g., too low). Therefore, it may be desirable to use a starter culture to adjust the number of microorganisms to the desired amount or concentration. In certain embodiments, the starter culture may be obtained by placing a thawed amount of a previously frozen aliquot containing glycerol and the selected microorganism into a Luria Bertani medium or other rich growth medium. In certain embodiments, the starter culture may be made by adding an agar stab of an agar plate containing the selected microorganism(s) and/or a streak of a single colony from a plate containing the selected microorganism(s) to a suitable rich growth media. The selected microorganism(s) present in the starter cultures may then be grown by incubating the starter culture at a suitable temperature for 8 to 16 hours or longer. Suitable temperatures may be from 32° to 39° C., 34 to 38° C., or even 37° C., depending on the microorganism(s) selected. In some instances, the starter culture may require anaerobic incubation in a controlled environment suitable for the growth of the selected microorganism(s). When incubating the starter culture, it may be desirable to minimize evaporation of liquid from the starter culture, for example, by controlling the humidity of the environment and/or covering the starter culture vessel with a liquid impermeable material (e.g., lid or film material). It may also be desirable to control other environmental factors such as the levels of carbon dioxide and nitrogen.

The starter culture may be harvested within 24 hours after inoculation with the selected microorganism(s). The timeframe for the harvest of the starter culture should correspond to the transition from the logarithmic growth phase of the starter culture to the stationary growth phase, as is well known in the art. To begin harvesting, the starter culture may be centrifuged at a speed that is sufficient to pelletize the microorganism cells but still maintain viability (e.g., between 5000 and 10,000×g for 15 minutes at 4° C.). Upon centrifugation, the supernatant should be completely denayted. The pellet of microorganism cells may be washed with a saline solution to remove undesirable contaminants left over from the complex media. The denayted and, optionally, washed cells may be re-suspended in a medium of choice (e.g., a minimal carbon medium) to provide a work culture with a suitable amount and/or concentration of the selected microorganism(s) for screening the test agent(s). In certain embodiments, the work culture may be between a 1× and a 100× (e.g., 10×) dilution of the starter culture. The concentration of cells in the starter and/or work culture may be calculated by any means known to those in the art (e.g., correlating an optical density value obtained with a spectrophotometer to a cell count).

After the selected microorganism(s) have been re-suspended in the work culture, one or more samples (e.g., 1, 2, 3, 4, 5, 6, 7, 8, 9, 10 or more, but typically less than 100) are removed from the work culture and placed in a suitable reaction vessel. Reaction vessels are known in the art and include, without limitation, multi-well vessels, single-well vessels, one or more tubes, conventional test plates (e.g. 12-well plate, 96-well plate, 384-well plate, 1536-well plate), and the like. The sample size may be determined by the size of the reaction vessel and/or the concentration of microorganisms. It is important to ensure that a suitable amount of the selected microorganism is included in the sample from the work culture. For example, 0.1 ml of a 10× dilution work solution may be placed in each well of a suitable 96-well plate. In order to screen a test agent, the microorganism(s) must be exposed to the test agent. Thus, the test agent and the sample of the work culture are combined to form a test sample. The test agent(s) may be added directly to the reaction vessel before, after, or at the same time as the sample from the work culture. Additionally or alternatively, the test agent(s) may be combined with the work culture and/or one or more elements thereof prior to being placed in the reaction vessel. The ratio of the test agent(s) to the test sample may be any standard dilution such as 1:10, with care taken to ensure that there is sufficient room in the test vessel to add the microorganisms. It is important to provide the appropriate ratio because if too much test agent is provided, it may become toxic to the microorganism. On the other hand, if too little test agent is provided the sensitivity of the assay may be undesirably affected.

Assays to Identify a Test Agent as a Prebiotic

To determine if the test agent is a prebiotic or may have prebiotic potential, one or more measurements are taken to determine how the microorganism(s) react to a test agent. It may be desirable to take such measurements at predetermined times (e.g., at 0, 24, 48, 72, 96 and/or 120 hours after providing the test sample), time intervals of, for example, 1, 2, 3, 4, 5, 6, 7, 8, 9, 10 or more hours) and/or combinations of these. It is to be appreciated that the foregoing examples of time and time intervals are not particularly limiting and any suitable time or time interval may be used, as desired.

In some embodiments, an ATP assay may be utilized in conjunction with a minimal carbon medium and one or more skin commensal microorganisms. It has been discovered that an ATP assay is particularly well suited for use as high thruput screening method, either singly or as part of tiered screening methodology, for compounds having prebiotic potential for one or more skin commensal microorganisms. ATP levels can be measured very quickly in a multi-well plate (e.g., less than 15 or 20 minutes), making it very well suited for screening hundreds or thousands of compounds for prebiotic potential very quickly. These compounds can then be screened further with more time and/or resource intensive methods (e.g., plate count) to refine the candidate pool of compounds having prebiotic potential. ATP assays have traditionally been correlated to plate count increases, meaning the inherent amount of ATP measured per bacterial cell under a given culture condition is relatively constant and therefore increases in cell number correlate with increases in ATP. Thus, a common endpoint historically assessed by ATP is correlating an increase in cell count for a given increase in ATP. When screening for compounds or materials having prebiotic potential herein, however, the primary inquiry is not cell count but rather the amount of metabolic activity that is present (which may or may not lead to an increase in cell count). While not intending to be bound by any theory, it is believed that when under metabolic distress in the presence of a minimal carbon media, cell ATP levels will decrease/plateau. These "hungry" cells will be primed for a prebiotic food source and begin metabolizing ATP in its presence, which may or may not lead to an increase in cell count. As such, it can be desirable to follow an ATP assay with a low thru put assay, such as plate count, in a tiered screening methodology to assess cell count/growth in the presence of a compound or material having been identified as having prebiotic potential in an ATP assay. The plate count assay, while slower and more resource intensive, provides a confirmatory assessment of the robustness of the prebiotic potential of a test compound.

Figures 11, 12:
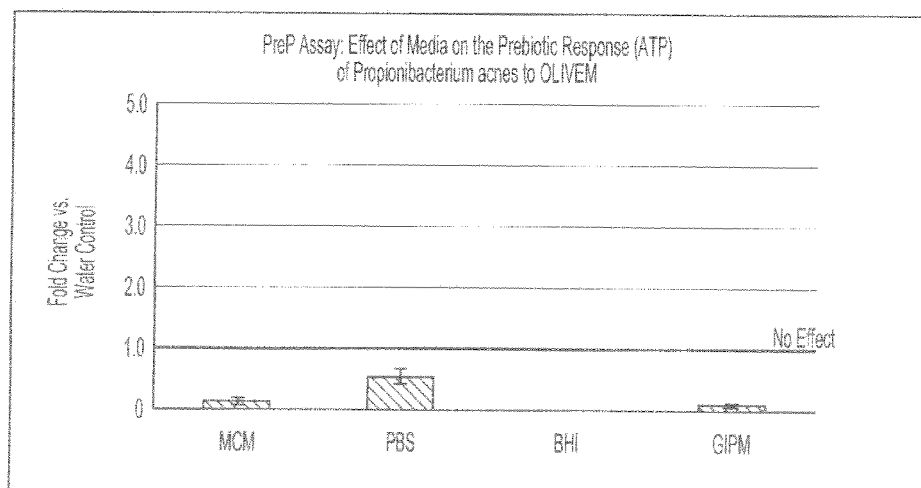
FIG. 11 illustrates a comparison between an ATP assay and a variety of conventional assays.
FIG. 12 illustrates the effect of OLIVEM on P. acnes.

In addition to their suitability for assessing prebiotic potential quickly for a variety of skin commensal microorganisms, ATP assays also have a good detection threshold for use in a prebiotic screening method utilizing skin commensal microorganisms. FIG. 11 illustrates a comparison between an ATP assay and a variety of conventional assays for *C. jeikeium, S. epidermidis* and *P. acnes*. As illustrated in FIG. 11, the ATP assay provides a fast detection time of 15 minutes and a detection limit that is second only to the much slower plate count assay. Thus, the ATP assay provides a fast detection time and suitable sensitivity for use as a high thru-put screening assay.

In use, the amount of ATP or other metabolite in a test sample may be measured to obtain a test value that is indicative of the metabolite level. The test value may be compared to a corresponding control value to determine if there was any change in the metabolism of the microorganism. If the test value is greater than the corresponding control value, then the test agent is identified as a prebiotic or as having prebiotic potential. The control value may be obtained by measuring the amount of ATP in a control culture (e.g., formed by suspending the selected microorganism(s) in a minimal carbon medium), or the control value may be a previously calculated or measured value. In certain embodiments, the control value may be obtained by measuring the ATP level in the work culture or the test sample at a time point of 0 minutes (i.e., within 30 minutes of re-suspending the microorganisms in the work culture and/or immediately after providing the test sample in the test vessel). The ATP and/or other metabolite level in the test sample and/or control may be measured according to any suitable method known in the art. One particularly suitable way to measure ATP level is with a BacTiter-GLO Microbial Cell Viability Assay, available from Promega Corporation Madison, Wis. The BacTiter-GLO Microbial Cell Viability Assay contains reagents that may be used to drive the oxidation of luciferin under catalysis by luciferase, resulting in the emission of light. The amount of emitted light is measured with a luminometer to provide a value that corresponds to the amount of ATP present.

Instead of an ATP assay, in some embodiments, it may be desirable to measure the replication level of the selected microorganism(s) (e.g., with a conventional plate count assay known to those skilled in the art) to determine whether a test agent is a prebiotic. A change in the replication level of the test sample may be assessed by comparing the number and/or concentration of microorganisms in the test sample to a control value. If the comparison indicates that an increase in replication level has occurred, then the test agent is identified as a prebiotic or as having prebiotic potential. The number and/or concentration of microorganisms in the test sample may be measured to obtain a test value by measuring the optical density of the test sample, an amount of DNA present in the test sample by PCR, performing a limiting dilution analysis, performing an enzyme-linked immunosorbent assay, performing a direct microscopic count, labeling the microorganism with a light-emitting or colored compound and measuring the luminescence or color, and/or any other suitable means known in the art. The control value may be obtained by measuring the number and/or concentration of microorganisms in a control culture (e.g., the selected microorganism(s) suspended in a minimal carbon media), or the control value may be a previously calculated or measured value. In certain embodiments, the control value may be obtained by measuring the number and/or concentration of microorganisms in the work culture or the test sample at a time point of 0 minutes.

Assay to Identify a Test Agent as a Broad Spectrum Prebiotic or as a Selective Prebiotic In some instances, it may be desirable to determine whether a single test agent or combination of test agents can increase the metabolism and/or replication of more than one species of microorganism ("broad spectrum prebiotic"), and in particular two or more skin commensal microorganisms. One reason for this may be due to variability in the microbiome observed between individuals and sites. In certain embodiments, it may be desirable to exploit the excellent sensitivity of an MCM to screen for one or more test agents that exhibit prebiotic activity on one or more particular skin commensal microorganisms, but not on other skin commensal microorganisms. It is recognized in the art that the presence of certain microorganisms on certain portions of the body may be undesirable. For example, it may be undesirable to promote the growth of *P. acnes* on the skin of a person's face since *P. acnes* is generally associated with the occurrence of acne. But it may be desirable to promote the growth of *S. epidermidis* on the skin of a person's face. Thus, in this example, it would be desirable to identify test agents that exhibit prebiotic activity on *S. epidermidis* but not *P. acnes*. Once such a selective prebiotic is identified, it can be incorporated into a cosmetic composition, especially a skin care composition, for use on the face to potentially improve the health of facial skin.

When identifying a broad spectrum prebiotic or a selective prebiotic, it may be necessary to prepare a work culture for each microorganism to be tested. Each work culture will include at least one microorganism that is not present in the other culture(s). For example, the assay may include a first culture inoculated with *C. jeikeium*, a second starter culture inoculated with *S. epidermidis*, and a third starter culture inoculated with *P. acnes*. Additionally or alternatively, the assay may include a first starter culture inoculated with *C. jeikeium* and *S. epidermidis* and a second starter culture inoculated with *S. epidermidis* and *P. acnes*. In yet another example, the assay may include a first starter culture inoculated with *C. jeikeium* and a second starter culture inoculated with *S. epidermidis* and *P. acnes*. The work cultures may be formed as described above. One or more test samples from the work culture are placed in a suitable test vessel with at least one test agent. The metabolism and/or replication of the microorganism(s) in each test sample is measured to determine if the test agent exhibits prebiotic activity on one or more of the test samples, as discussed above. If the test agent exhibits prebiotic activity on more than one microorganism (i.e., the metabolite and/or replication levels measured in each of two test samples are both greater than a control value) then the test agent is identified as a broad spectrum prebiotic. If the test agent exhibits prebiotic activity on at least one skin commensal microorganism and does not exhibit prebiotic activity on at least one other skin commensal microorganism, then the test agent is a selective prebiotic.

Figure 13:
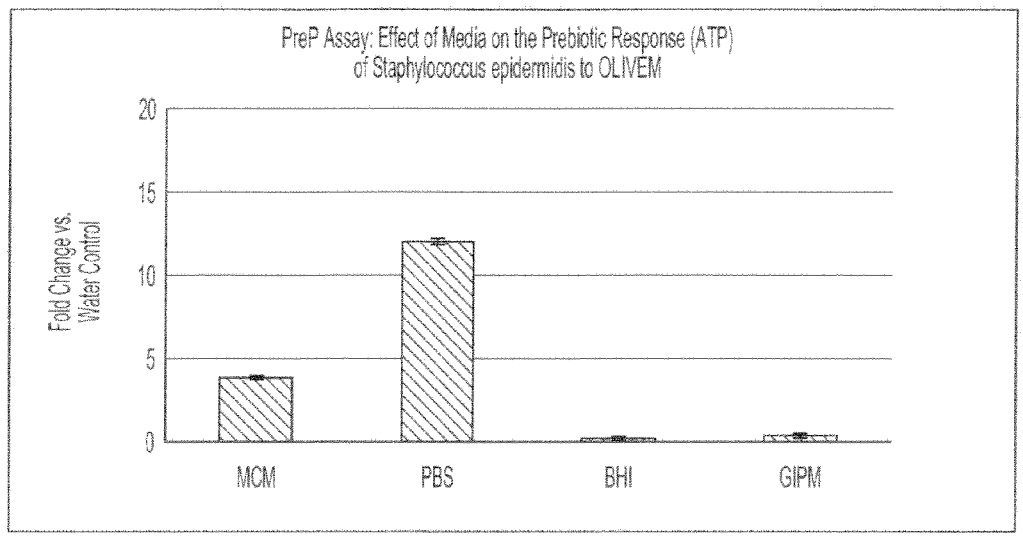
FIG. 13 illustrates the effect of OLIVEM on S. epidermidis.
Figure 14:
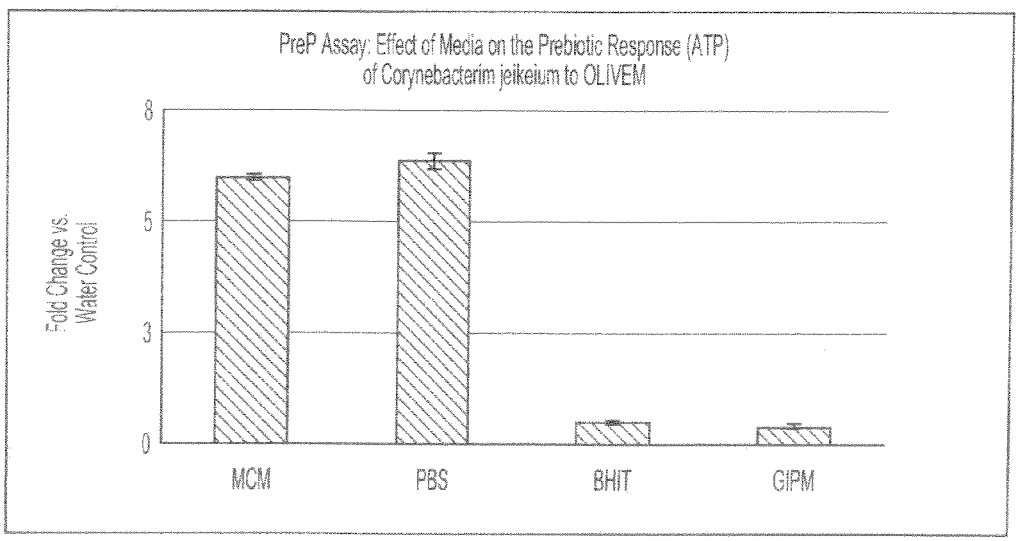
FIG. 14 illustrates the effect of OLIVEM on C. jeikeium.

FIGS. 12-14 illustrate the ability of the present assay to identify a test agent with selective prebiotic potential. In these examples, the test agent is an emulsifying agent sold under the trade name OLIVEM 450, available from the B&T Company, Italy. The prebiotic potential, or lack thereof, of OLIVEM 450 with regard to *P. acnes, S. epidermidis* and *C. jeikeium* is demonstrated by measuring the ATP level of each microorganism relative to a water control. As can be seen in FIG. 12, OLIVEM appears to have no or very little prebiotic potential with regard to *P. acnes*. On the other hand, as illustrated in FIGS. 13 and 14, respectively, OLIVEM 450 appears to have at least some prebiotic potential for *S. epidermidis* and substantial prebiotic potential for *C. jeikeium*, when used in conjunction with an MCM. Thus, the present assay may be exploited to identify test agents that have no, some, or substantial prebiotic potential with regard to one or more particular skin commensal microorganisms.

High-Throughput, Tiered Assay

The number of potential prebiotic agents is vast, and prior to the discovery of the present high-throughput, tiered assay there was no suitable method in the art for predicting which test agents might exhibit in vivo prebiotic activity (i.e., prebiotic activity when placed on the skin of a living person). As a result, each test agent had to be tested in vivo to determine if it exhibited suitable prebiotic activity. However, testing even a single agent in vivo can be expensive and time consuming, and testing a large number of agents in vivo is commercially impractical. Certain in vitro methods for screening test agents, such as conventional plate count methods may require less time and resources than in vivo methods, but even the in vitro methods may be commercially impractical for screening large libraries of test agents. For example, a typical plate count assay may require hundreds of plates and from 1 to 4 days to obtain an indication of in vitro prebiotic activity. Measuring metabolite levels such as ATP level provides a relatively fast (e.g., 15 minutes) way to screen large libraries of test agents, but may result in undesirable false positives and/or false negatives. A false positive or false negative is a false indication that a suitable level of prebiotic activity is either present or absent, respectively. Thus, using an ATP assay alone may result in identifying test agents as prebiotics that do not exhibit the desired level of activity in vivo.

It has been found that by using a tiered assay approach, large libraries of test agents can be screened in a relatively short amount of time and still provide a desirable level of predictability as to whether a test agent will exhibit in vivo prebiotic activity. It will be appreciated that a wide variety of screening methods may be combined into a tiered screening methodology using the teachings herein. In a tiered approach, a large initial number of test agents can be selected and screened relatively quickly, for example, with an ATP assay (or other measurement of metabolic indicator level) to identify agents that have prebiotic potential. Since an ATP assay utilizing an MCM is intended to measure metabolic activity and may not necessarily be correlative of cell count or other end points relevant to prebiotic potential, it may be desirable to follow an initial ATP assay screen with a secondary assay such as plate count. In addition, a second screening assay is beneficial as it is possible that some false positives and/or false negatives may be identified by the first screening method. The test agents that exhibit prebiotic potential in the first assay are then screened through the second assay to refine which test agents are most likely to provide the desired level of in vivo prebiotic activity. For example, an initial library of 1000 test agents may be screened with an ATP assay that identifies 10 agents as having prebiotic potential. In this example, the 10 prebiotic agents may then be screened with a plate count assay that identifies 2 particularly suitable prebiotic agents that are most likely to provide the desired prebiotic activity in vivo. Continuing with this example, the two particularly suitable prebiotic agents may be tested in vivo to confirm the predictive results of the high-throughput, tiered assay. Thus, in this example, a library of 1000 test agents can be greatly reduced to a much smaller number of candidates for in vivo testing, which provides a more commercially practical approach from the perspective of time and resource investment.

Cosmetic Compositions.

Because of the health and/or appearance benefit provided by a healthy, balanced skin microbiome, it may be desirable to incorporate prebiotic agents into a cosmetic composition. That is, it may be desirable to include a prebiotic agent as an ingredient in the cosmetic composition. In certain embodiments, the cosmetic composition may include a dermatological acceptable carrier, a prebiotic, and one or more optional ingredients of the kind commonly included in the particular cosmetic compositing being provided. For example, the cosmetic composition may include a skin care active useful for regulating and/or improving the condition of mammalian skin. Nonlimiting examples of such optional ingredients include vitamins; peptides and peptide derivatives; and sugar amines. Other optional ingredients include sunscreen actives (or sunscreen agents) and/or ultraviolet light absorbers. In certain embodiments, the cosmetic composition may include a colorant, a surfactant, a film-forming composition, and/or a rheology modifier. Suitable cosmetic compositions herein may be in any one of a variety of forms known in the art, including, for example, an emulsion, lotion, milk, liquid, solid, cream, gel, mouse, ointment, paste, serum, stick, spray, tonic, aerosol, foam, pencil, and the like. The cosmetic compositions may also be incorporated into shave prep products, including, for example, gels, foams, lotions, and creams, and include both aerosol and non-aerosol versions. Other cosmetic compositions include antiperspirant, deodorant, and personal cleaning compositions such as soap and shampoo.

Compositions incorporating prebiotic agents identified by using the novel methods described herein may be generally prepared according to conventional methods known in the art of making compositions and topical compositions. Such methods typically involve mixing of ingredients in or more steps to a relatively uniform state, with or without heating, cooling, application of vacuum, and the like. For example, emulsions may be prepared by first mixing the aqueous phase materials separately from the fatty phase materials and then combining the two phases as appropriate to yield the desired continuous phase. In certain embodiments, the compositions may be prepared to provide suitable stability (physical stability, chemical stability, photostability, etc.) and/or delivery of active materials. The composition may be provided in a package sized to store a sufficient amount of the composition for a treatment period. The size, shape, and design of the package may vary widely. Some package examples are described in U.S. Pat. Nos. D570,707; D391,162; D516,436; D535,191; D542,660; D547,193; D547,661; D558,591; D563,221; and U.S. Publication Nos. 2009/0017080; 2007/0205226; and 2007/0040306.

EXAMPLES

The following are non-limiting examples of various aspects of the methods described herein. The examples are given solely for the purpose of illustration and are not to construed as limiting the invention, as many variations thereof are possible.

Example 1

Example 1 demonstrates that media selection can be a variable for determining whether a test agent exhibits prebiotic activity. In this example, three different classes of media are compared for their effect on *C. jeikeium, S. epidermidis*, and *P. acnes*. The *C. jeikeium, S. epidermidis*, and *P. acnes* are obtained from American Type Culture Collection (ATCC) in Manassas, Va. as Catalog Nos. 43734, 12228, and 11827, respectively. The first class of media is represented by a conventional rich growth medium used to grow each of the three microorganisms. The second class of media is represented by Gastrointestinal Prebiotic Medium ("GIPM"), which is a medium commonly used for testing with gastrointestinal microorganisms. GIPM is made from peptone water, bile salts, NaCl, $NaHCO_3$, $K_2HPO_4$, Tween 80, $KH_2PO_4$, hemin, $MgSO_4.7H2O$, vitamin K1, $CaCl_2.6H2O$, and cystein.HCl. The third class of media is represented by an MCM suitable for use with the novel methods disclosed herein. The MCM is made from NaCl, $(NH_4)_2HPO_4$, $K_2HPO_4$, and $MgSO_4$ and has a pH of between 6.8 and 7.2.

The three different microorganisms are each grown in a starter culture using sterile media, which may be sterilized using conventional methods (e.g., autoclave). *S. epidermidis* is grown in a starter culture of brain heart infusion media ("BHI"); *C. jeikeium* is grown in a starter culture of BHI media supplemented with 0.1% Tween 80 ("BHIT"); and *P. acnes* is grown in a starter culture of reinforced clostridial broth ("RCB"). The BHI media is made by adding 37 grams of a commercially available powder of peptic digest of animal tissue, sodium chloride, dextrose, pancreatic digest of gelatin, and disodium phosphate to 1 liter of USP water. The RCB is made by adding 38 grams of a commercially available powder of casein enzymatic hydrolysate, beef and yeast extract, dextrose, sodium chloride, sodium acetate, starch, and 1-cysteine hydrochloride to 1 liter of USP water. Glycerol stock inoculums of each of the three kinds of bacteria are prepared by mixing 0.75 ml of a log culture with 0.25 ml of 80% glycerol and storing at −80° C. until use. On day 1, the starter culture of BHIT is made by inoculating the BHIT media in a 50:1 ratio with *C. jeikeium* in a suitable vessel (i.e., 1 ml glycerol stock inoculum to 50 ml BHIT media). Also on day 1, the starter culture of RCB is made by inoculating the RCB media in a 50:1 ratio with *P. acnes* in a suitable vessel (i.e., 1 ml glycerol stock inoculum to 50 ml RCB media). The starter culture containing *C. jeikeium* is incubated aerobically at 37° C. for 46 to 48 hours. The starter culture containing *P. acnes* is incubated anaerobically at 37° C. for 46 to 48 hours. On day 2, the starter culture of BHI is made by inoculating the BHI media in a 50:1 ratio with *S. epidermidis* in a suitable vessel (i.e., 1 ml glycerol stock inoculum to 50 ml BHI media) followed by aerobic incubation at 37° C. for 22 to 26 hours.

On day 3, the three starter cultures are harvested by room-temperature centrifugation at a speed sufficient to pelletize the bacteria but maintain viability (e.g., 8500 rpm in a Sorvall Evolution RC centrifuge). The bacterial pellets from the starter cultures are washed in a 0.90% w/v saline solution ("normal saline"), re-pelleted as per harvest, and then re-suspended in enough normal saline to provide a work culture with a bacterial concentration of between $0.5 \times 10^7$ CFU/ml to $5 \times 10^8$ CFU/ml. The test materials are distributed in a suitable reaction vessel (i.e., any vessel that can be sampled from, such as a flask or a 96-well plate) to provide test samples. In this Example, the test samples are made by adding 1 part test material to 8 parts test media to 1 part work culture. For example, the test samples may be made by combining 0.1 ml of test material, 0.8 ml of test media, and 0.1 ml of work culture to each well of a 96-well, deep-well plate. The test materials in this example are 10× test agent stock solutions containing either beet pulp in water or OLIVEM 450 in water. A water control sample may be prepared by replacing the test agent in the test sample with water. For example, a water control sample may be made by adding 1 part water to 8 parts test media to 1 part work culture. The time at which the test materials are added to the reaction vessel is T=0, which in this Example is when the test materials are placed in a well of the 96-well, deep-well plate to form a test sample. The test media for *C. jeikeium* is MCM, BHIT, PBS and GIPM. The test media for *S. epidermidis* is MCM, BHI, PBS and GIPM. The test media for *P. acnes* is MCM, RCB, PBS and GIPM. All transfers of media or other ingredients may be performed, for example, by using an Eppendorf Research Series Adjustable Volume Pipetter, volume 100 μl to 1000 μl or volume 2 μl to 20 μl, available from Fisher Scientific, Pittsburgh, Pa. Each test condition is performed in triplicate. Prior to sampling a well for a measurement, the contents of each well are mixed by pipetting up and down in the well, which is a conventional mixing technique known in the art. To measure the ATP in each well, a portion of the test sample is removed from each well of the reaction vessel using a suitable transfer apparatus and placed in a 96-well, black well plate (e.g. 100 microliters). Optionally, enough glucose may be added to the wells containing *S. epidermidis* to reach a final concentration of 1% v/v and waiting at least 5 minutes at room temperature. It is believed, without being limited by theory, that *S. epidermidis* tends to use up its ATP faster than the other two microorganisms when stressed (i.e., starved). Thus, adding glucose may "prime" the *S. epidermidis* and provide a baseline ATP level that is commensurate with a corresponding plate count value. However, it may be desirable to refrain from adding glucose to the wells containing the *S. epidermidis* in order to potentially increase the dynamic range for measurable prebiotic activity. After placing the test sample portion in the black-well plate, the ATP level of the test sample is determined by adding an equal volume of ATP reagent (e.g., BacTiter Glo, from Promega Corporation) to each well. For example, a 100 ul test sample portion would get 100 ul of ATP reagent according to the manufacturer instructions. The plates are then incubated at room temperature for fifteen minutes with shaking at 750 rpm. The luminescence of the cultures should be measured using a suitable luminescent plate reader (for example, Victor X Multi Label Plate Reader, Wallac/PerkinElmer, Waltham, Mass.) and the corresponding luminescence recorded as an ATP response. The ATP level of the test samples is determined at T=0, T=24 hours and T=48 hours. The ATP level measured at T=0 is determined as soon as possible after making the test samples, and in no event longer than 30 minutes. For plate count assessments, 10 μl from each triplicate reaction vessel is removed at T=0, for a total of 30 ul, and placed in 970 ul of normal saline, serially diluted as needed to allow a countable range of 20-300 colonies per plate, and then plated on duplicate *Brucella* blood agar plates by adding 50 ul of appropriate dilutions on each plate. The resultant plates are incubated at 33-37° C. in the presence of oxygen or 35-37° C. anaerobically (depending on whether the microorganism prefers aerobic or anaerobic conditions) and analyzed 48 to 72 hours later using conventional colony counting techniques known in the art to determine the number of CFUs.

FIGS. 5-10 demonstrate the ability to measure a fold change in ATP or colony counts in the test samples of Example 1 compared to a corresponding water control sample. The ATP level or colony counts of each sample at T=48 hours is compared to the corresponding value at T=0 to determine the change from baseline value. The change from baseline value of the test sample is then compared to the change from baseline value of the corresponding water control sample to get a treatment effect fold change. Fold change refers to the number of times there is a 100% increase (or decrease). Thus, a two-fold change is a 200% change, a three-fold change is a 300% change, etc.

Figure 5:
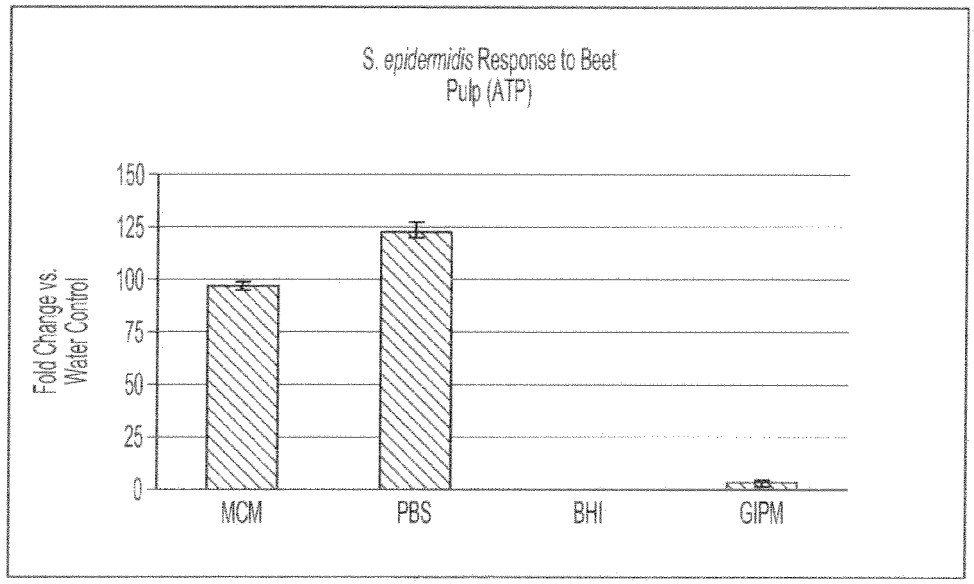
FIG. 5 illustrates a change in the amount of ATP induced by a test agent on S. epidermidis.
Figure 6:
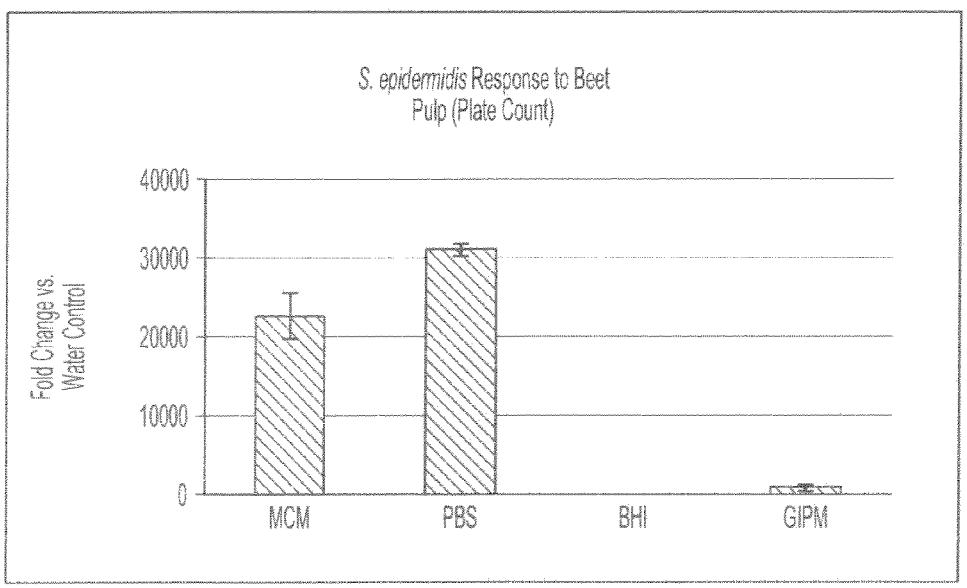
FIG. 6 illustrates a change in colonies induced by a test agent on S. epidermidis.

FIG. 5 illustrates the effect of MCM, PBS, BHI and GIPM on the ability to measure a fold change in the ATP level of *S. epidermidis* upon contact with beet pulp relative to a water control. The test samples contain beet pulp as the test material, *S. epidermidis*, and the test media indicated in FIG. 5. The beet pulp was replaced by distilled water to make the water control samples. The change from baseline ATP value was determined by comparing the change in ATP level at T=0 and T=48 for the test sample and the control. The change from baseline ATP value of the test sample was compared to the change in baseline ATP value for the control to determine the fold change. As illustrated in FIG. 5, the MCM and PBS test media provide significantly higher sensitivity than the BHI and GIPM test media as demonstrated by the significantly higher fold change in measured ATP level. FIG. 6 illustrates the effect of MCM, PBS, BHI and GIPM on the ability to measure a fold change in the number of *S. epidermidis*, when measured by a standard plate count, upon contact with beet pulp, relative to a water control. As illustrated in FIG. 6, the plate count measurement confirms that the ATP results shown in FIG. 5 may be used to suitably predict the prebiotic activity of a test agent.

Figure 7:
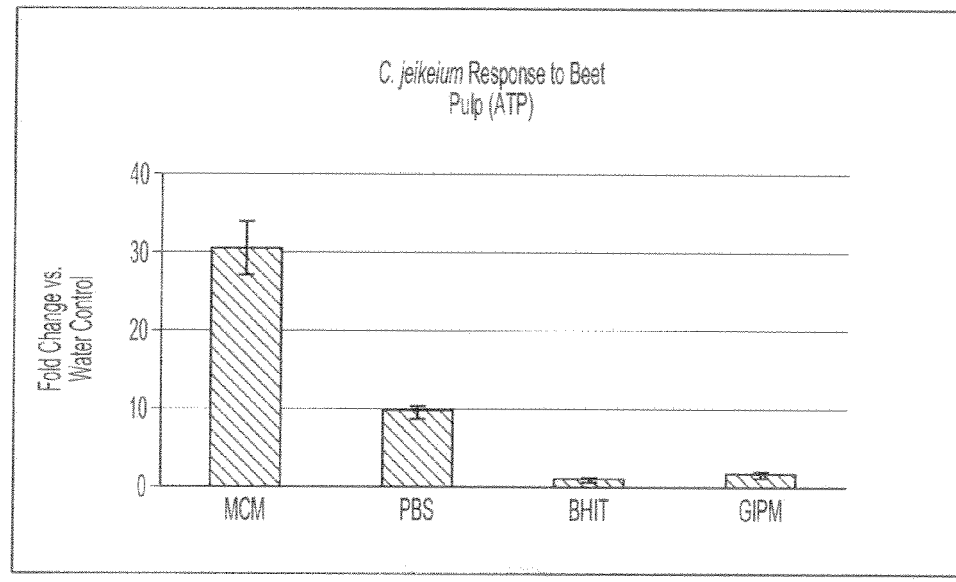
FIG. 7 illustrates a change in the amount of ATP induced by a test agent on C. jeikeium.
Figure 8:
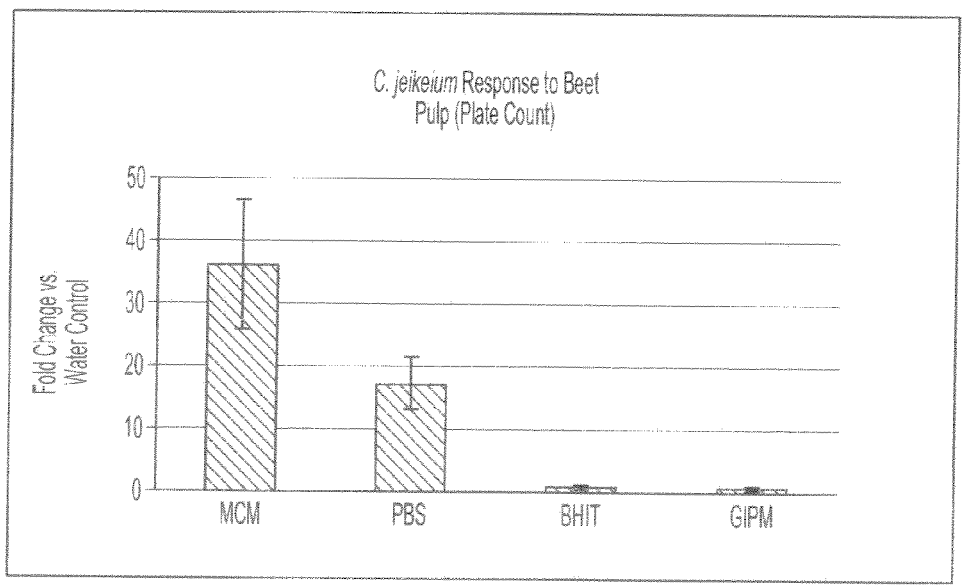
FIG. 8 illustrates a change in colonies induced by a test agent on C. jeikeium.

FIG. 7 illustrates the effect of MCM, PBS, BHIT and GIPM on the ability to measure a fold change in the ATP level of *C. jeikeium* upon contact with beet pulp relative to a water control. As illustrated in FIG. 7, the MCM and PBS test media provide significantly higher sensitivity than the BHIT and GIPM test media as demonstrated by the significantly higher fold change in measured ATP level. FIG. 8 illustrates the effect of MCM, PBS, BHIT and GIPM on the ability to measure a fold change in the number of *C. jeikeium*, when measured by a standard plate count, upon contact with beet pulp, relative to a water control. As illustrated in FIG. 8, the plate count measurement confirms that the ATP results shown in FIG. 3 may be used to suitably predict the prebiotic activity of a test agent. The fold changes illustrated in FIGS. 7 and 8 were determined in the same way as the fold changes illustrated in FIGS. 5 and 6.

Figure 9:
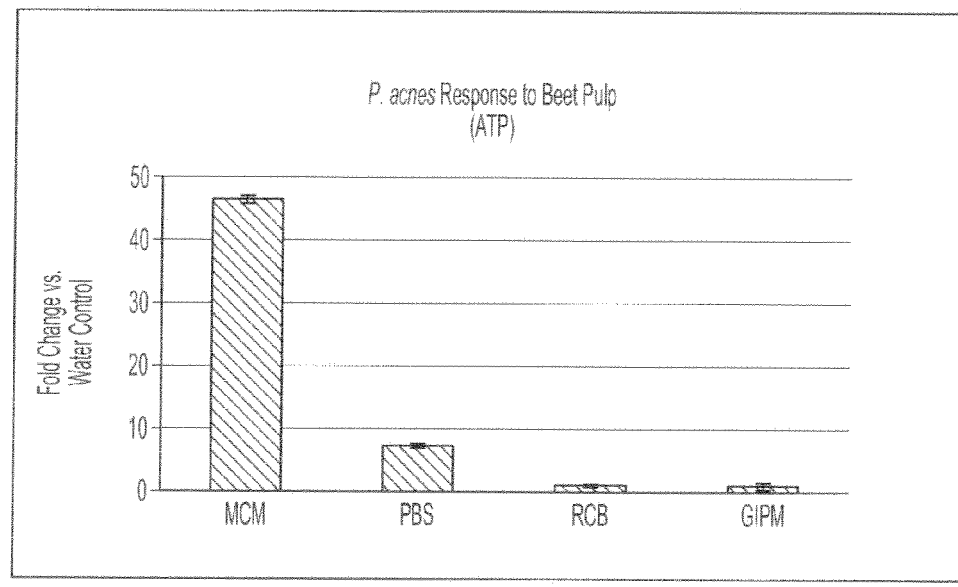
FIG. 9 illustrates a change in the amount of ATP induced by a test agent on P. acnes.
Figure 10:
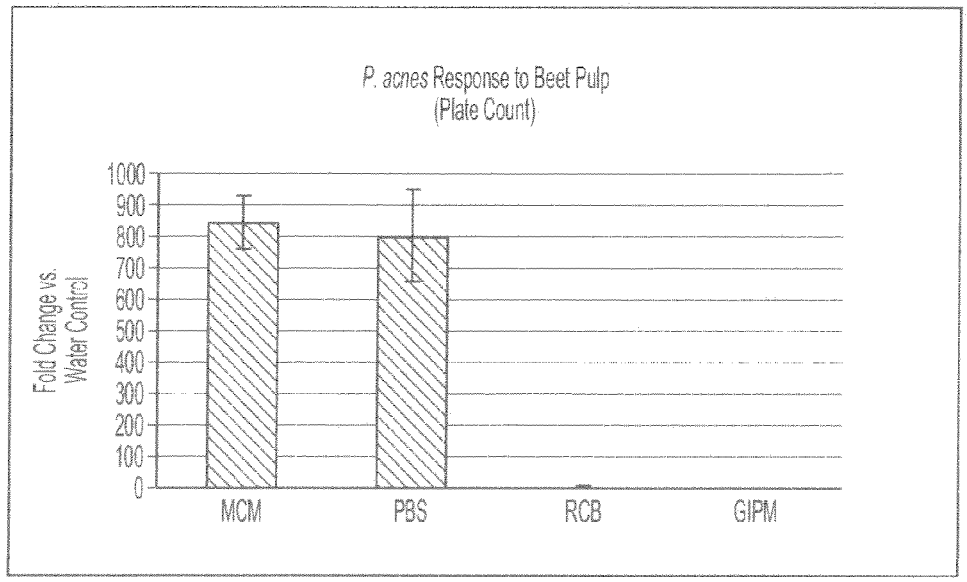
FIG. 10 illustrates a change in colonies induced by a test agent on P. acnes.

FIG. 9 illustrates the effect of MCM, PBS, RCB and GIPM on the ability to measure a fold change in the ATP level of *P. acnes* upon contact with beet pulp relative to a water control. As illustrated in FIG. 9, the MCM and PBS test media provide significantly higher sensitivity than the RCB and GIPM test media as demonstrated by the significantly higher fold change in measured ATP level. FIG. 10 illustrates the effect of MCM, PBS, RCB and GIPM on the ability to measure a fold change in the number of *P. acnes*, when measured by a standard plate count, upon contact with beet pulp, relative to a water control. As illustrated in FIG. 8, the plate count measurement confirms that the ATP results shown in FIG. 7 may be used to suitably predict the prebiotic activity of a test agent. The fold changes illustrated in FIGS. 9 and 10 were determined in the same way as the fold changes illustrated in FIGS. 5 and 6.

From FIGS. 5-10, it is to be appreciated that the present minimal carbon media provide a greater dynamic range of measurable prebiotic potential of the test agent and in some cases is the only medium where the prebiotic potential of a test agent can be observed. These results demonstrate the unexpected benefit of minimal carbon media providing improved sensitivity when screening test agents for prebiotic activity on human skin commensal microorganisms.

Example 2

Example 2 compares the results of an ATP assay to a plate count assay. The plate count assay is a generally accepted assay known in the art for measuring growth or survival of cultivable bacteria in a culture. While plate counts can be a useful tool to identify prebiotic materials, it is considered a low-throughput, resource intensive method for prebiotic assessment and predicting whether a test agent will exhibit in vivo prebiotic activity on human skin commensal microorganisms. In contrast, using the ATP assay as a pre-screening tool provides increased through-put and substantially less resources when screening test agents for prebiotic activity. Furthermore, ATP results are generally predictive of plate count results, and thus it is believed that the results of the ATP assay are reliable enough to provide an initial screening method for quickly identifying prebiotic candidates for further testing.

Example 2 utilizes starter cultures of *C. jeikeium, S. epidermidis*, and *P. acnes* prepared and harvested as described in Example 1 above. The harvested starter cultures were used to make work cultures, which were transferred to reaction vessels, also as described in Example 1 above. An MCM was prepared as described in Example 1, and 8 parts of the MCM was added to each well. 10× test agent stock solutions were prepared by mixing appropriate weights or volumes of stock materials with USP grade water to make a stock solution (10×). These stock solutions were passed through a 0.2 micron filter to remove contaminating bacteria. One part test agent stock solution was then added to 8 parts MCM to provide a test sample. Water (USP) was used as a control. Twenty-five test agents were screened. The test agents were BIOAGAVE brand inulin, available from GTC Nutrition; Bac-Lyte brand banana extract available from Mark Lyte; Purimune brand galacto-oligosaccharide ("GOS") available from GTC Nutrition; rice bran available from Kirin, Japan; short-chain oligofructose (Oligofructose P95); Nutriose FB06 brand wheat dextrin, available from Roquette; Canadian Harvest Oat Fiber 610, available from SunOpta; beet pulp; gentio-oligosaccharide, available from Wako Pure Chemicals; Isomalto 500 brand isomalto-oligosaccharide, available from Showa Sango, Vivinal GOS 15 brand galacto-oligosaccharide; Promilin Fengreek extract (hydroxyisoleucine), available from TSI Health Sciences; Zyactinase 45 brand kiwi extract, available from Vital Foods; Solactis brand galactofructose, available from Solvay; BIMUNO brand galacto-oligosaccharide, available from Clasado; konjac glucomannan hydrolysates, available from Glycologic Limited, UK; Nutraflora brand Short-chain fructo-oligosaccharides (scfox P95), available from GTC Nutrition; C☆IsoMaltidex™ brand polyol sugar alcohol, available from Cargill; raffinose pentahydrate; Biomyox brand nasturtium officinale extract, available from SILAB, France; Perenityl PG brand hexyldecanol/pear seed extract, Vincience, France; Dermochlorella D brand *Chlorella vulgaris* extract, available from Barnet Products; Promatrixyl brand palmitoyl pentapeptide-3, available from Sederma, France; eutanol G16 brand 2-hexyldecanol; and Phlorogine BG brand Laminaria saccharina extract, available from Biotechmarine, France. Another test agent, which was not tested by which may be suitable for use herein is Pitera (a yeast ferment filtrate of sake). Each test condition was performed in triplicate for ATP and duplicate for plate counts. The contents of each well were mixed and sampled for each appropriate assay. For example, for ATP, 100 microliters of each sample was placed in wells of a shallow, black well plate. Enough glucose was also added to the wells containing S. epidermidis to reach a final concentration of 1% (v/v) and incubated at room temperature for at least 5 minutes. An equal volume of BacTiter-GLO reagent (Promega Corporation, Madison, Wis.) was added to each well of the black well plate. The plates were then incubated at room temperature for fifteen minutes with shaking at 750 rpm. The luminescence of the cultures was subsequently measured using a Victor X Multi-Label Plate Reader (available from PerkinElmer, Waltham, Mass.). Additionally, samples of each reaction vessel were removed and diluted serially in normal saline as appropriate to reach a countable range of bacteria on each plate (e.g. 1:10 to 1:10,000) and then plated on duplicate appropriate agar plates for bacteria tested (e.g., TSA, TSA-0.1% Tween, RCA). All plates were incubated at 37° C. in the presence of oxygen or anaerobically at 37° C. as appropriate and analyzed 48 to 72 hours later.

Of the 25 test agents examined, 22 test agents increased the levels of ATP in S. epidermidis cultures, 21 test agents increased the levels of ATP in C. jeikeium cultures, and 22 test agents increased the levels of ATP in P. acnes cultures, as compared to the water only controls. Of the 25 test agents, 23 test agents increased the number of CFUs present in S. epidermidis cultures, 11 test agents increased the number of CFUs present in C. jeikeium cultures, and 24 test agents increased the number of CFUs present in P. acnes cultures, as compared to the water only controls. The plate count and ATP assays agreed on 20 test agents used with S. epidermidis, 15 test agents used with C. jeikium, and 22 test agents used with P. acnes. However, the ATP assay was found to produce several false negatives. In particular, 2 test agents used with S. epdermidis and 3 test agents used with P. acnes were found to not influence the ATP levels, but did influence the replication of the bacteria as assessed by plate counts. The ATP assay was also found to produce several false positives. In particular, 2 test agents used with S. epidermidis, 10 test agents used with C. jeikeium, and 1 test agent used with P. acnes were found to increase the levels of ATP in these cultures, but did not appear to affect the replication of the bacteria as assessed by plate counts. It is important to note that false positives, while not desirable, are not as undesirable as false negatives. This is because false positives are tested again via plate count, which typically provides the proper characterization of the test agent. Additionally, the false positives provide an indication that the ATP assay may be decoupled from the plate count assay. That is, the ATP assay may be used as an independent and/or early indicator of prebiotic activity, as opposed to the conventional usage of the ATP assay, which is to simply correlate ATP to the number of microorganisms present in the sample.

Table 1 illustrates the results of using an ATP assay to screen the twenty-five test agents of Example 2 for prebiotic activity. As can be seen in Table 1, the ATP assay provides a suitable indication of prebiotic activity with regard to S. epidermidis, C. jeikeium and P. acnes, which demonstrates that the ATP assay, when used in tandem with a plate count assay, may provide a reliable screening method for identifying test agents that are likely to exhibit in vivo prebiotic activity.

TABLE 1

| | S. epidermidis | C. jeikeium | P. acnes |
|---|---|---|---|
| Number of test agents that induced an increase in the levels of ATP | 22 | 21 | 22 |
| Number of test agents that induced an increase in the number of colony forming units | 23 | 11 | 24 |
| Number of test agents where there was an agreement between the ATP and plate count methods | 20 | 15 | 22 |
| Number of false negatives displayed by the ATP assay | 2 | 0 | 3 |
| Number of false positives displayed by the ATP assay | 2 | 10 | 1 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. A method of making a topical cosmetic composition, the method comprising:
   (a) providing a first culture comprising a test agent, a quantity of a human skin commensal microorganism, and a minimal carbon medium;
   (b) determining a metabolite level or a replication level of the human skin commensal microorganism of the first culture;
   (c) comparing the metabolite level or the replication level to a first control value, wherein the first control value is the metabolite level or replication level in a culture of the human skin commensal microorganism of the first culture that is grown without the test agent, and wherein the metabolite level correlates with the amount of growth;
   (d) identifying the test agent as a prebiotic when the test agent increases the growth of the human skin commensal microorganism and when the metabolite level or replication level of the first culture is greater than the first control value; and
(e) combining a safe and effective amount of the prebiotic with a dermatologically acceptable carrier.

2. The method of claim 1, further comprising incorporating an ingredient selected from the group consisting of vitamins, peptides, peptide derivatives, sugar amines, sunscreen agents, ultraviolet light absorbers, colorants, surfactants, film-forming compositions, rheology modifiers and combinations thereof into the cosmetic composition.

3. The method of claim 1, wherein the minimal carbon medium has a carbon content of between about 0.001% and 0.1% by weight, based on the weight of the medium.

4. The method of claim 1, wherein the minimal carbon medium has a carbon content of less than 0.001% by weight, based on the weight of the media.

5. The method of claim 1, wherein the minimal carbon medium comprises NaCl, $(NH_4)_2HPO_4$, $K_2HPO_4$, and $MgSO_4.7H_2O$.

6. The method of claim 1, wherein the minimal carbon medium includes a supplement selected from the group consisting of iron, biotin, nicotinic acid, D-pantothenic acid, pyridoxal, pyridoxamine dihydrochloride, thiamine hydrochloride, glucose, galactose,
mannose, fructose, sucrose, lactose, maltose and combinations thereof.

7. The method of claim 1, wherein the minimal carbon medium is free of valine and arginine.

8. The method of claim 1, wherein the microorganism exhibits less than a 0.2 log increase in the number of CFUs after 24 hours in the minimal carbon medium.

9. The method of claim 1, wherein the metabolite level of the first culture is determined by measuring an amount of ATP present in the first culture with an ATP assay.

10. The method of claim 1, wherein the replication level is determined by a method selected from the group consisting of optical density measurement, DNA measurement by PCR, plate count, limiting dilution analysis, enzyme-linked immunosorbent assay, direct microscopic count, and labeling the microorganism with a light-emitting or colored compound and measuring the luminescence or color.

11. The method of claim 1, wherein the test agent comprises a botanical.

12. The method of claim 1, wherein the test agent comprises a microbial lysate.

13. The method of claim 1, wherein the human skin commensal microorganism is a species in one of the following genera: *Staphylococcus, Corynebacterium* or *Propionibacterium.*

14. The method of claim 1, further comprising:
(a) providing a second culture that includes the test agent, a quantity of a second human skin commensal microorganism which is different from the first human skin commensal microorganism, and the minimal carbon medium;
(b) determining a second metabolite level or a replication level of the second culture;
(c) comparing the second metabolite level or the replication level of the second culture to a second control value, wherein the second control value is the second metabolite level or replication level in a culture of the human skin commensal microorganism of the second culture that is grown without the test agent, and wherein the second metabolite level correlates with the amount of growth; and (d) identifying the test agent as a selective prebiotic when the test agent decreases the growth of the second human skin commensal microorganism and when the metabolite level or the replication level in the first culture is greater than the first control value and the metabolite level or the replication level in the second culture is less than the second control value.

15. The method of claim 14, further comprising:
(a) providing a third culture that includes the test agent, a quantity of a third human skin commensal microorganism that is different from the first and second human skin commensal microorganisms, and the minimal carbon medium; and
(b) identifying the test agent as a selective prebiotic when the test agent increases or decreases the growth of the third human skin commensal microorganism and when the metabolite level of a third metabolite or the replication level of the third culture is greater than or less than the third control value, wherein the third control value is the third metabolite level or replication level in a culture of the human skin commensal microorganism of the third culture that is grown without the test agent, and wherein the third metabolite level correlates with the amount of growth.

16. The method of claim 1, further comprising:
(a) providing a second culture that includes the test agent, a quantity of a second human skin commensal microorganism which is different from the first human skin commensal microorganism, and the minimal carbon medium;
(b) determining the metabolite level or a replication level of the second culture;
(c) comparing the metabolite level or the replication level of the second culture to a second control value, wherein the second control value is the metabolite level or replication level in a culture of the human skin commensal microorganism of the second culture that is grown without the test agent; and
(d) identifying the test agent as a broad spectrum prebiotic if the test agent increases the growth of the second human skin commensal microorganism and if the metabolite level or the replication level of the first and second cultures is greater than the first and second control values, respectively.

17. The method of claim 16, further comprising:
(a) a third culture that includes the test agent, a quantity of a third human skin commensal microorganism that is different from the first and second human skin commensal microorganisms, and the minimal carbon medium; and
(b) identifying the test agent as a broad spectrum prebiotic if the metabolite level or the replication level of the third culture is greater than the third control value, wherein the third control value is the metabolite level or replication level in a culture of the human skin commensal microorganism of the third culture that is grown without the test agent.

18. A method of making a topical cosmetic composition, the method comprising:
(a) providing a culture that includes a test agent and a quantity of a human skin commensal microorganism;
(b) determining a metabolite level of the culture;
(c) comparing the metabolite level of the culture to a first control value, wherein the first control value is the metabolite level in a culture of the human skin commensal microorganism culture that is grown without the test agent, and wherein the metabolite level correlates with the amount of growth;

(d) performing a plate count assay using the culture when the metabolite level of the culture is greater than the first control value, wherein the greater metabolite level results from the test agent increasing the growth of the human skin commensal microorganism;

(e) comparing the number of colonies present in the plate count assay to a second control value, wherein the second control value is the number of colonies in a plate count assay of a culture of the human skin commensal microorganism that is grown without the test agent;

(f) identifying the test agent as a prebiotic agent if the number of colonies present in the plate count assay of step (d) is greater than the second control value; and (g) combining a safe and effective amount of the prebiotic agent with a dermatologically acceptable carrier.

* * * * *